(12) United States Patent
Schonhardt et al.

(10) Patent No.: US 9,554,837 B2
(45) Date of Patent: Jan. 31, 2017

(54) DEVICE FOR FIXING AN ELONGATE ELEMENT IN A RETAINING STRUCTURE

(71) Applicant: Medartis AG, Basel (CH)

(72) Inventors: Jürgen Schonhardt, Rheinfelden (DE);
Thomas Tribelhorn, Rünenberg (CH);
Hermann Zeuner, Freiburg (DE);
Joanna Norström, Basel (CH)

(73) Assignee: Medartis AG, Bassel (CH)

( * ) Notice: Subject to any disclaimer, the term of this patent is extended or adjusted under 35 U.S.C. 154(b) by 0 days.

(21) Appl. No.: 14/546,241

(22) Filed: Nov. 18, 2014

(65) Prior Publication Data

US 2015/0142065 A1    May 21, 2015

Related U.S. Application Data

(62) Division of application No. 12/110,785, filed on Apr. 28, 2008, now abandoned.

(30) Foreign Application Priority Data

May 3, 2007    (EP) .................................... 07107464

(51) Int. Cl.
| | |
|---|---|
| *A61B 17/80* | (2006.01) |
| *A61B 17/62* | (2006.01) |
| *A61B 17/84* | (2006.01) |
| *A61B 17/86* | (2006.01) |
| *A61B 17/34* | (2006.01) |

(52) U.S. Cl.
CPC ............ *A61B 17/8047* (2013.01); *A61B 17/62* (2013.01); *A61B 17/848* (2013.01); *A61B 17/861* (2013.01); *A61B 17/864* (2013.01); *A61B 90/50* (2016.02); *A61B 2017/3405* (2013.01); *A61B 2017/868* (2013.01); *A61B 2017/8655* (2013.01)

(58) Field of Classification Search
CPC ... A61B 17/8047; A61B 17/848; A61B 17/62; A61B 17/861; A61B 2017/868; A61B 2017/3405; A61B 19/26; A61B 17/864
USPC ........... 606/301, 313–314, 316, 55, 57, 290, 292,606/309, 305, 296
See application file for complete search history.

(56) References Cited

U.S. PATENT DOCUMENTS

| | | |
|---|---|---|
| 388,000 A | 8/1888 | Rider |
| 1,151,861 A | 8/1915 | Brumback |
| 2,135,637 A | 11/1938 | Gade |
| 2,136,524 A | 11/1938 | Rosenberg |

(Continued)

FOREIGN PATENT DOCUMENTS

| | | |
|---|---|---|
| CA | 2405235 | 2/2001 |
| DE | 3439795 | 6/1985 |

(Continued)

*Primary Examiner* — Paul Prebilic
(74) *Attorney, Agent, or Firm* — Davis & Bujold PLLC; Michael J. Bujold (57) ABSTRACT

A fixation device is used to fix an elongate element, in particular a wire, in an opening of a retaining structure, in particular of an implant plate. The fixation device has a main body. The main body is provided with a bore for receiving the elongate element. The main body is radially deformable in a clamp area, such that the diameter of the bore can be reduced. The main body has an outer contour which is designed in such a way that, when the fixation device is inserted into the opening of the retaining structure, the clamp area is deformed such that the elongate element is clamped securely in the bore.

17 Claims, 9 Drawing Sheets

(56) References Cited

U.S. PATENT DOCUMENTS

| | | | |
|---|---|---|---|
| 2,284,847 A | 6/1942 | Raymond | |
| 2,346,346 A | 4/1944 | Anderson | |
| 2,479,698 A | 8/1949 | Paquin | |
| 4,095,914 A | 6/1978 | Thomsen | |
| 4,127,119 A | 11/1978 | Kronner | |
| 4,135,505 A | 1/1979 | Day | |
| 4,347,636 A | 9/1982 | Capuano et al. | |
| 4,620,533 A | 11/1986 | Mears | |
| 4,621,627 A | 11/1986 | DeBastiani | |
| 4,858,601 A | 8/1989 | Glisson | |
| 4,890,631 A | 1/1990 | Hardy | |
| 4,941,481 A | 7/1990 | Wagenknecht | |
| RE33,348 E | 9/1990 | Lower | |
| 5,242,252 A | 9/1993 | Harle | |
| 5,275,601 A | 1/1994 | Gogolewski et al. | |
| 5,290,288 A | 3/1994 | Vignaud et al. | |
| 5,393,161 A | 2/1995 | Mata et al. | |
| 5,393,191 A | 2/1995 | Alexander | |
| 5,407,295 A | 4/1995 | Kuhl et al. | |
| 5,456,719 A | 10/1995 | Keller | |
| 5,601,553 A | 2/1997 | Thalgott et al. | |
| 5,674,036 A | 10/1997 | Hsieh | |
| 5,702,394 A | 12/1997 | Henry et al. | |
| 5,709,686 A | 1/1998 | Talos et al. | |
| 5,807,396 A | 9/1998 | Raveh et al. | |
| 5,993,450 A | 11/1999 | Worcel | |
| 6,322,562 B1 | 11/2001 | Wolter | |
| 6,572,622 B1 | 6/2003 | Schafer et al. | |
| 6,702,814 B2 | 3/2004 | Walulik et al. | |
| 6,716,214 B1 | 4/2004 | Jackson | |
| 6,730,091 B1 | 5/2004 | Pfefferle et al. | |
| 7,981,142 B2 | 7/2011 | Konieczynski et al. | |
| 2001/0021851 A1 | 9/2001 | Eberlein et al. | |
| 2001/0035075 A1 | 11/2001 | Amis et al. | |
| 2002/0045901 A1 | 4/2002 | Wagner et al. | |
| 2002/0128655 A1 | 9/2002 | Michelson | |
| 2003/0040746 A1* | 2/2003 | Mitchell | A61B 17/1606 623/17.11 |
| 2003/0078583 A1 | 4/2003 | Biedermann et al. | |
| 2003/0149429 A1 | 8/2003 | Ferrante et al. | |
| 2003/0171754 A1 | 9/2003 | Del Medico et al. | |
| 2003/0187439 A1 | 10/2003 | Biedermann et al. | |
| 2004/0059330 A1 | 3/2004 | Biedermann et al. | |
| 2004/0073218 A1 | 4/2004 | Dahners | |
| 2004/0260292 A1 | 12/2004 | Orbay et al. | |
| 2005/0038521 A1 | 2/2005 | Hormansdorfer et al. | |
| 2005/0043736 A1 | 2/2005 | Mathieu et al. | |
| 2005/0143742 A1 | 6/2005 | Porcher | |
| 2005/0165400 A1 | 7/2005 | Fernandez | |
| 2005/0216003 A1 | 9/2005 | Biedermann et al. | |
| 2006/0058797 A1 | 3/2006 | Mathieu et al. | |
| 2006/0142766 A1 | 6/2006 | Schafer | |
| 2006/0195104 A1* | 8/2006 | Schlafli | A61B 17/60 606/291 |
| 2007/0043366 A1 | 2/2007 | Pfefferle et al. | |
| 2007/0055240 A1 | 3/2007 | Matthis et al. | |
| 2007/0083207 A1 | 4/2007 | Ziolo et al. | |
| 2007/0225715 A1 | 9/2007 | Deffenbaugh et al. | |
| 2014/0228895 A1* | 8/2014 | Ziolo | A61B 17/8047 606/290 |
| 2016/0270831 A1* | 9/2016 | Perrow | A61B 17/1671 |

FOREIGN PATENT DOCUMENTS

| | | | |
|---|---|---|---|
| DE | 19629011 | 1/1998 | |
| EP | 517939 | 12/1992 | |
| EP | 1202675 | 5/2002 | |
| EP | 1306057 | 5/2003 | |
| EP | 1408859 | 4/2004 | |
| EP | 1570796 | 9/2005 | |
| EP | 1571971 | 9/2005 | |
| EP | 1736109 | 12/2006 | |
| EP | 1741396 | 1/2007 | |
| GB | 2031731 | 4/1980 | |
| JP | 63158308 | 7/1988 | |
| JP | 3046729 | 5/2000 | |
| WO | 01/12081 | 2/2001 | |
| WO | 03/065911 | 8/2003 | |
| WO | 03/105704 | 12/2003 | |
| WO | 2004/086990 | 10/2004 | |
| WO | 2005/013840 | 2/2005 | |
| WO | WO2005013840 A1 * | 2/2005 | A61B 17/60 |
| WO | 2007/036807 | 4/2007 | |
| WO | 2008/055648 | 5/2008 | |
| ZA | 9306875 | 4/1994 | |

\* cited by examiner

DEVICE FOR FIXING AN ELONGATE ELEMENT IN A RETAINING STRUCTURE

This application is a division of copending application Ser. No. 12/110,785, filed May 3, 2007.

BACKGROUND OF THE INVENTION

The invention relates to a fixation device, a combination of such a fixation device with an elongate element, and a corresponding arrangement with a retaining structure, and an osteosynthesis set, as described below.

Various types of fixation devices are used in bone surgery. In various indications, an elongate element, for example a Kirschner wire, has to be secured on a retaining structure, for example an internal or external fixator. Various arrangements are known for securing the wires in the retaining structure.

U.S. Pat. No. 4,941,481 and U.S. Pat. No. 4,620,533, for example, disclose clamp-like devices which can be guided in the manner of a clamping jaw over an elongate element and in so doing fix the latter. U.S. Pat. No. 6,702,814 discloses a clamping device which can be used for an external fixator and in which two clamping jaws form a channel for receiving an elongate element. One of the clamping jaws is elastically deformable in order to receive the elongate element.

U.S. Pat. No. 5,393,191 discloses an external fixator in which an elongate element can be guided into a slotted ball that can be pressed in between two clamping jaws. The orientation of the elongate element received in the ball can be adjusted in this way.

A surgical guide body is known from EP 1 202 675. The guide body is used to receive fixation elements and for this purpose has a plurality of openings inclined relative to one another. By means of an intermediate piece, a longitudinal fixation element, for example a wire, can be fixed by pressing, clamping or friction.

Other fixation devices for elongate elements are known from U.S. Pat. No. 2,346,346, U.S. Pat. No. 4,890,631, U.S. Pat. No. 5,702,394, EP 1 408 859, WO 03/105704, EP 1 736 109, EP 1 570 796, U.S. Pat. No. 4,621,627, EP 1 741 396, EP 1 306 057, U.S. Pat. No. 4,135,505, U.S. Pat. No. 4,127,119 or DE 3439795, WO 03/065911.

However, all these known solutions are associated with various disadvantages. In particular, many of the known solutions are made up of a plurality of individual elements. Production and use is therefore complicated and also expensive. A further disadvantage of known solutions is that the elongate elements to be fixed can often be secured only in one direction, or they can be secured in different directions only by means of structurally complex solutions.

It is true that EP 1 202 675 discloses a solution in which a position is possible in different directions without complicated ball joints. However, different directions are in this case also only possible in a defined and limited number according to preformed, inclined openings of the guide body. A correction of the direction is not possible.

SUMMARY OF THE INVENTION

It is therefore an object of the present invention to avoid the disadvantages of the known solutions, in particular therefore to make available a fixation device for fixing elongate elements which is easy and inexpensive to produce and can be handled in a simple manner. The fixation device is nonetheless intended to allow the direction of the elongate element to be selected as freely as possible and, if appropriate, to be corrected. A further object of the present invention is to make available a corresponding fixation device that can be repositioned in a simple manner, for example for fixing an elongate element at a different angle than originally provided.

A further object of the present invention is to make available such a fixation device in combination with an elongate element, and an arrangement with such a combination and with an additional retaining structure, which also meet the abovementioned objects.

A further aspect of the invention additionally concerns an osteosynthesis set made up of at least two implant plates. When treating osteoporotic bone in particular, a problem that often arises is that implant plates with threaded screws cannot be anchored sufficiently securely in the bone substance. According to this aspect of the invention, it is an object to make available an osteosynthesis set which is suitable for solving the known problems, in other words which permits a secure fixation of the implant plates even when insufficient or unsuitable bone substance means that conventional fixation with a screw is not possible or the hold of the screw does not provide adequate stability.

According to the invention, these objects are achieved with a fixation device, with a combination of such a fixation device and an elongate element, with an arrangement having such a combination, and with an osteosynthesis set as described below.

The fixation device according to the invention is used to fix an elongate element, in particular a wire, pin, tube or a thread, in a seat of a retaining structure. The retaining structure is typically a plate. However, the term retaining structure is to be interpreted widely. Applications are also conceivable in which the retaining structure primarily applies the clamping forces described below, and is not used for actually holding the fixation device. The fixation device has a main body. The main body is provided with an opening, in particular a continuous bore, for receiving the elongate element. The opening can extend in the longitudinal direction. It is also conceivable, however, to provide openings in the transverse direction (i.e. at an angle of more than 0° to the longitudinal axis) of the main body, for example for distraction. While the opening for receiving the elongate element is typically round (when used to receive cylindrical objects such as wires), other shapes of the opening are also conceivable. For example, a slit-shaped opening for receiving planar elongate elements is also conceivable. Differently shaped openings for receiving profiled elongate elements are also conceivable.

According to the invention, the main body, at least in an outer clamp area, is radially deformable such that the dimension of the opening, in particular the diameter of the bore, can be reduced. In the context of the present application, outer clamp area is to be understood as that area in which the main body is compressed by contact with the seat in the retaining structure. The main body additionally has an outer contour which is designed in such a way that, when the fixation device is inserted into the opening of the retaining structure, the clamp area can be deformed radially such that the elongate element can be clamped securely in the opening. Viewed in the direction of the elongate element, the secure clamping can be effected axially at the same height at which the clamp area is arranged. It is also conceivable, however, to provide for the elongate element to be clamped axially at a distance from the outer clamp area of the main body. Before insertion into the retaining structure, the elongate element can easily be inserted into the opening of the main body. When inserting the main body into the seat of the retaining structure, the main body is radially compressed by virtue of the specific configuration of its outer contour. In this way, the elongate element is securely clamped in the opening of the main body, such that it can no longer be displaced in the axial direction. The solution according to the invention is particularly simple, since, in addition to the elongate element and the retaining structure, only one additional component (the fixation device) is necessary for fixing the elongate element.

According to a first preferred embodiment of the invention, the fixation device is provided, in its clamp area, with at least one slit. The slit extends at least partially in the direction of the opening and ends at least partially in the opening. The slit can reach as far as the outer wall of the fixation device. The slit does not necessarily have to extend in a plane and instead can have one or more bends or curves. By virtue of this at least one slit, the main body can be radially compressed particularly easily. One slit may itself be sufficient. However, any desired greater number of slits can also be provided. The slit or slits are arranged in the radial direction for example. However, it is also conceivable to provide areas of weakening in the main body by means of tangential or curve-shaped slits. The slit typically extends exactly in the direction of the opening for receiving the elongate element. However, it is also conceivable to provide the slit at angles relative to the axis of the fixation device. Alternatively, however, it is also conceivable for the main body to be made of an elastic material. In this case, a radial compression can be achieved even without a slit. In addition, in order to simplify the insertion of the elongate element, the main body can also be made up of several mutually movable parts. Two parts connected by a hinge are conceivable. These parts can be opened out for insertion of the element and then closed again and connected to each other. The axial fixation of the elongate element is then effected once again in the manner described above.

In addition, it is also conceivable for the main body to be made from several materials and with several components. For example, elastic material could be used for the clamp zone, and tough material for the locking zone and screwdriver zone. Such a fixation device can be produced, for example, by multi-component injection molding.

According to another preferred embodiment, the fixation device, at least in the clamp area, is provided on its outer contour with at least one clamp surface. The clamp surface at least partially widens radially, seen in the circumferential direction. A main body with such a structure, but without an elongate opening and without slits, is known from WO 04/086990 for locking a bone screw in an implant plate. The contour of the outer surface which can be described in an azimuth plane by part of a logarithmic spiral, by part of a circular trajectory, by part of an involute or the like and known from WO 04/086990 is expressly incorporated into the present application by reference thereto. When the screw head with the clamp surfaces is brought by means of rotation into contact with corresponding wedge projections of a seat of a retaining structure, radial forces arise that lead to a compression of the main body. It has been found that such a locking screw is particularly suitable for fixation of elongate elements if it is provided with an elongate opening for receiving the element and with means for facilitating the radial compression, for example slits.

Moreover, the fixation device according to the invention particularly preferably has a main body which, seen in the longitudinal direction, has a rounded outer contour in the area of the clamp surface, in particular at least partially an approximately spherical, spiral, parabolic, elliptic or hyperbolic contour. A contour is generally preferred which allows the direction of the fixation device in a seat of a retaining structure to be adjusted in an almost unlimited manner within a defined angle range. No additional components such as ball joints, clamping jaws or the like are needed for this purpose. It is also conceivable, however, to provide a main body with a cylindrical or conical outer contour, if at the same time a retaining structure with a seat is made available which has a correspondingly rounded contour. The outer face of the main body and/or the seat of the retaining structure can additionally be structured, for example with fluting or knurling.

According to another preferred embodiment of the invention, the fixation device, at least in its clamp area, is designed as a screw head. The design as a screw head in particular permits simple rotation of the fixation device in the circumferential direction. In the above-described design with clamp surfaces widening radially in the circumferential direction, the radial compression can be achieved in a particularly simple manner by rotation using a screwdriver, for example with a cross-head, Torx, hexagon socket or variations thereof, for example the Applicant's "HexaDrive".

On its main body, the fixation device can additionally be provided with a screw shank with a screw thread. It is also conceivable, however, to additionally provide the fixation device with a shank of a pin. Therefore, depending on the application, it may be advantageous to use a fixation device composed exclusively of a main body, or a fixation device in which the main body is additionally provided with the shank of a pin or of a screw.

According to another preferred embodiment of the invention, the fixation device, when designed as a screw head in its clamp area, can additionally be provided with an extension above the clamp area. The extension is designed as a seat for a screwdriver. In this way, a torque can be applied particularly easily to the fixation device.

According to another preferred illustrative embodiment of the invention, the at least one slit, seen in the longitudinal direction of the fixation device, extends at least over the clamp area. It is also conceivable, however, for the slit or slits to extend over a longer axial area, in order to further increase the deformability and flexibility of the main body. At most, the slits extend along the entire length of the fixation device. By suitable choice of length of the slits, it is possible to adjust the clamping action on the elongate element.

According to another preferred embodiment of the invention, the inner surface of the opening can be structured. In this way, it is possible, by means of an additional form fit, to achieve increased retention in the axial direction as a result of the radial compression. In other words, this means that, with a given clamping force, a greater force would have to be applied to the elongate element in the axial direction in order to tear it from the fixation device.

In accordance with the above embodiments, one aspect of the invention is also that a locking screw known per se is additionally provided with a longitudinal bore and, in the area of the screw head, with at least one slit. It is particularly preferable here to use a locking screw of the type shown and claimed in US 2007/0043366. The subject matter of said application, and in particular of the claims of US 2007/0043366, is hereby expressly incorporated in the present application.

A further aspect of the invention therefore lies in the use of such a locking screw for fixation of an elongate element in a retaining structure. By using a multi-directional locking screw, however, the elongate element can also be fixed in the longitudinal direction in a defined angle position, which can be freely selected within a range of angles.

Yet another aspect of the invention concerns the combination of a fixation device as described above and an elongate element. The elongate element is selected from the group including wires, rods, pins, profiles, springs, hollow tubes, or an instrument for manipulation, for example a scalpel or spatula (e.g. for manipulations on the brain). If the elongate element is designed as a wire, rod or pin, applications are possible for example with an internal fixator or an external fixator. If the elongate element is designed as a profile or a hollow tube, applications as an endoscopy tube or for fixation of a drill guide are also conceivable, for example. If the elongate element is designed as a fixture for a scalpel, the fixation device according to the invention can additionally be used as scalpel holder for holding a scalpel. The shaft of the scalpel can be inserted into the elongate bore. In such an application, however, it is also conceivable not to provide a longitudinal bore in the fixation element, and instead to directly fit a part of the blade of the scalpel into slits present on the fixation element.

To increase the axial clamping effect, the elongate element can additionally have a structured surface.

It is also conceivable, depending on the application, to provide the elongate element with a thread or with knurling in the longitudinal direction or transverse direction or also to provide it with a drill helix.

According to another preferred embodiment, the elongate element can be provided with a tip which is designed as a lancet or trocar, or which is provided with a self-cutting or self-drilling thread.

A cable/cord is also conceivable as an elongate element for transmitting tensile forces or for connecting torn soft-tissue parts such as tendons or ligaments or for fixing bone fragments.

A further aspect of the invention concerns an arrangement composed of the above-described combination of a fixation device and an elongate element together with a retaining structure. The retaining structure has at least one seat for a fixation device.

The seat for the fixation device is particularly preferably provided with radially inwardly directed projections or tapers. These tapers, together with the clamp surfaces on the fixation device, lead to a radial compression of the main body. To permit the simplest possible multi-directional positioning of the fixation device and therefore also of the elongate element held therein, the opening is also preferably provided with an inner wall which, in the longitudinal direction, has at least partially an approximately spherical, spiral, parabolic, elliptic or hyperbolic shape.

In particular, the opening is designed in accordance with the disclosure and claims in US 2007/0043366.

The retaining structure can, for example, be designed as a retaining structure for an endoscopy tube, which is retained in the retaining structure by the fixation device. In this case, the elongate element is an endoscopy tube.

The retaining structure can also be designed as a temporary intraoperative support element, for example as a fixation ring for an arthrodesis set.

Typical temporary intraoperative applications are applications in which certain bones are intended to be fixed for a limited time. Before the end of the surgical intervention, the corresponding support structure is removed. Indications are, for example, arthrodesis or partial arthrodesis of the wrist, neurosurgery, osteotomies, correction of fractures, and minimally invasive interventions, for example transbuccal interventions or spinal column surgery. External fixator is understood as an application in which, following surgery, the stabilizing or fixing structures are used outside of the body for avoiding bone movements and therefore for healing fractures. It is also conceivable, however, to fix certain degrees of freedom of structures (e.g. two bones connected by a joint) and to leave other degrees of freedom of the same structure deliberately alone in terms of their mobility (dynamic external fixator). This permits early postoperative physiotherapeutic exercise for preventing adhesion of soft-tissue parts and stiffening of the affected joints. These can typically be osteotomies, corrections or fracture treatments. Application in a ring fixator is also conceivable, where several rings can be fixed to one another likewise by means of the fixation device according to the invention. A use in the treatment of fractures of the upper arm is also conceivable, where the ball of the joint is held with a threaded wire, and the position can be very finely adjusted via a nut that bears on the screw head (pull-push instrument).

The retaining structure can additionally be formed by a surgical frame which can be secured by the fixation device to an operating table, for example in neurosurgical applications for holding drill sleeves or guide sleeves or spatulas.

In an application as an internal fixator, the arrangement as an implant for avoiding bone movements and for healing fractures remains permanently in the body. Typical applications may be arthrodesis or partial arthrodesis, stiffening of the spine, treatment of long bones in proximity to the joints, the epiphysis, all osteotomies, corrections or fracture treatments, wire osteosynthesis, using a plate with at least one hole, or skeletal anchoring in orthodontics. A wire fixator or cable fixator for generating tensile forces in soft-tissue parts is also conceivable.

In an application as an endoscope, manipulations in the body can be performed via the bore in the fixation device (for example in neurosurgery, oral surgery, orthodontics or facial surgery, in particular in transbuccal interventions, or in surgery of the spinal column or of the pelvis).

In the three last-mentioned cases, the elongate element is typically a wire or a tube/sleeve. Finally, the retaining structure can also be designed as a holder for an instrument, such as a scalpel, and in this case the elongate element is the blade shaft of the scalpel or a part of the blade.

While surgical applications have primarily been described here, other applications of the fixation device according to the invention, of the combination with an elongate element, and of the arrangement according to the invention are also conceivable. For example, such constructions can be used as quick-coupling systems for K-wires/drills in driving or drilling machines, as clamping mechanisms for grip pieces, e.g. in electrosurgery or for bone distraction (e.g. of palate, alveolar ridge). In applications for distraction, the elongate element can, for example, be designed in two parts, one part having an inner thread and one part having an outer thread. A fixation device with two transversely bored main bodies is used to receive one of the parts respectively. If the main bodies are each anchored in a bone fragment, the parts can be secured and used for distraction.

Other applications are also conceivable, however, e.g. in the construction field, e.g. in shelving, scaffolding, pegging (optionally with axial compression) or for shoring.

A further aspect of the invention concerns an osteosynthesis set. The set is made up of at least two implant plates or of one implant plate with at least two sections. The implant plates or the sections each have at least one seat for receiving a connecting arrangement. The set additionally comprises such a connecting arrangement. The connecting arrangement can be inserted into a respective bore of the plates or of the sections. The implant plates can be connected to one another and stabilized by means of the connecting arrangement of the implant plates. The plates are prevented from moving relative to each other along the elongate element. The firm fixation results in a connection of one or more plates. Fragments are then repositioned and fixed on this structure. In the case of a plate with two sections, a connection of one section, for example a tab of a plate, to another plate section can be created. This can be advantageous, for example, when the connection between the two plate sections has to be designed, for clinical reasons, such that it can transmit only a slight load or indeed no load or, for clinical reasons, is removed after the connection is established.

By virtue of the connecting arrangement, two or more such implant plates can be secured/connected at several locations of a bone, even when the bone, on account of its size or structure (internal makeup), is not suitable for receiving a bone screw for fixation of the implant plates.

It is also conceivable, in this context, to provide implant plates with tab-like parts that are angled off. The connecting arrangement can then be secured in a seat in this tab. This is particularly advantageous when, for anatomical reasons, the connection described above is not possible with flat plates, for example because the planes in the area of the seat are not arranged relative to one another by an angle which is smaller than the pivoting angle of the fixation elements. The angled-off parts then form small units that offer a position that can be used for the connection.

The connecting arrangement particularly preferably comprises a fixation device of the type described above. In this way, clamping wires can be secured in a particularly easy way in the openings of the implant plates. For certain applications, for example cranial and maxillo-facial applications, it is also conceivable to skew the angle of the seat relative to the plate, that is to say to orient the axis of the seat not perpendicular to the plane of the plate. A positioning of the screws in a wider angle range can thus be achieved, e.g. in a range of 15° (30°-15°) to 45° (30°+15°) for a seat inclined by 30°. In thin plates in particular, the plate can be thickened locally in the area of the seat. In this way, space is created for the inclined arrangement of the locking contour in the seat.

Alternatively, however, it is also conceivable that the connecting arrangement comprises an elongate element with a thread at at least one end. In addition, the connecting arrangement is in this case provided with a connecting element, e.g. a nut, into which the thread can be screwed and by means of which the elongate element can be secured in one or both of the plates.

BRIEF DESCRIPTION OF THE DRAWINGS

The invention is explained in more detail below on the basis of illustrative embodiments and with reference to the drawings, in which:

FIGS. 12 to 19 show various embodiments of elongate elements that can be used in connection with the present invention.

DETAILED DESCRIPTION OF THE INVENTION

Figure 1:
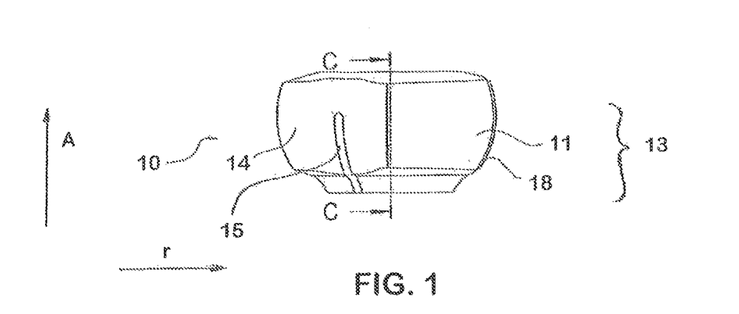
FIG. 1 shows a side view of a fixation device according to the invention.

FIG. 1 shows a fixation device 10 according to the invention in a side view. The fixation device 10 has a main body 11. The main body 11 is a seat of a retaining structure, for example can be inserted into the seat 63 in an implant plate 61, e.g. according to FIG. 6. The main body has a clamp area 13. In the clamp area 13, the main body 11 can be compressed by contact with the inner wall 65 of the seat (see FIG. 6). The main body 11 additionally has slits 15 extending in the axial direction A. Because of the slits 15, the main body 11 can be compressed in the radial direction r (i.e. in a plane perpendicular to the axial direction A). The main body 11 has an outer contour 14. The outer contour 14, at least in an area 18, is rounded when viewed in a direction perpendicular to the axial direction A. By means of the rounded outer contour 18, the main body or fixation device can be inserted into a seat 63 in a large number of different angle positions.

Figure 2A:
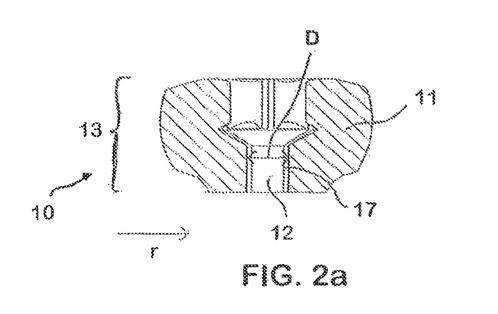
FIG. 2a shows a cross section of a fixation device according to FIG. 1, along the plane C-C.
Figure 2B:
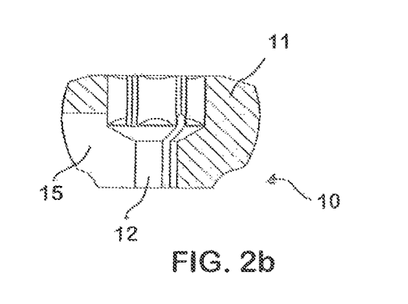
FIG. 2b shows a cross section through a plane along a slit of the fixation device.

The main body 11 is additionally provided with a bore 12 (see FIGS. 2a and 2b). The bore 12 is used to receive an elongate element. The diameter D of the bore 12 can be reduced by compression in the radial direction r. In this way, an elongate element, typically a wire, inserted into the bore 12 is securely clamped. To increase the clamping action, the inner surface 17 of the bore 12 can additionally be provided with a surface structuring.

FIG. 2b shows a cross section through the main body 11 in a plane along the slit 15. As FIG. 2b shows, the slit 15 extends from one edge of the main body 11 as far as the bore 12.

Figure 3:
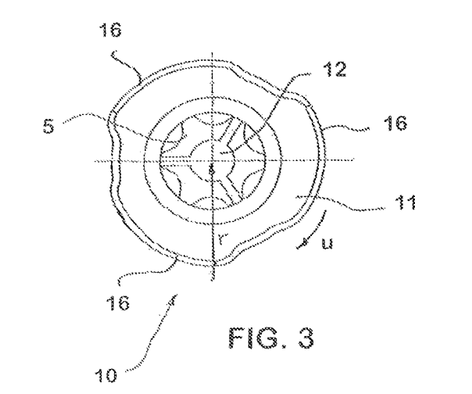
FIG. 3 shows a plan view of the fixation device according to FIG. 1.
Figure 4:
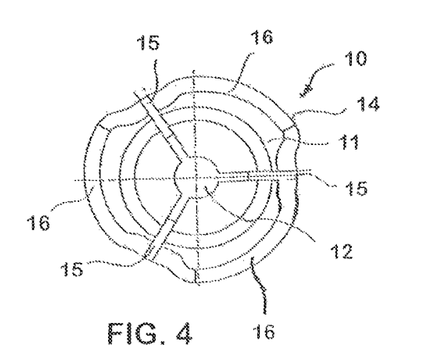
FIG. 4 shows a bottom view of the fixation device according to FIG. 1.

As FIGS. 3 and 4 show, the outer contour of the main body 10, in a plane perpendicular to the axial direction A, is provided with three clamp surfaces 16. The clamp surfaces 16 widen radially, seen counter to the circumferential direction U. If the main body 11 is inserted into a correspondingly designed opening with radial projections 64 (see FIG. 6) and is turned in the circumferential direction U, the clamp surfaces 16 come into engagement with the projections 64. This results in a compression in the radial direction.

To generate a rotation movement, the main body 11 is additionally provided, in the area of the bore 12, with a seat 5 for a corresponding tool, for example a screwdriver.

FIG. 4 shows a bottom view of the three slits 15, which are offset by 120° to one another and which extend exactly radially in FIG. 4. Other geometries of the slits are of course conceivable. As FIG. 1 shows, the slits 15 extend approximately along two thirds of the height of the main body 11. Of course, other dimensions of the slits in the longitudinal direction are also conceivable. It is also conceivable for the slits to be curved or tangential.

In medical applications, the fixation device according to the invention is made of a biocompatible material. Typically, titanium can be used. Other materials are also conceivable, such as stainless or bioabsorbable materials. It is also possible to use alloys with shape-memory properties, for example Nitinol or generally superelastic materials, and for example also plastic.

The dimension of the fixation device according to the invention depends on the particular field of application. Typically, for applications in the surgical field, fixation devices with a diameter of ca. 2 to 7 mm, bores with a diameter of ca. 0.75 to 1.4 mm and fixation devices with an overall height of ca. 1 to 5 mm are conceivable. The slits can typically have a slit width of 0.2 to 0.3 mm and extend over a height of 0.3 to 1.5 mm. Variations are of course conceivable, depending on the field of application, for example in spinal surgery where endoscopes with diameters of 10-50 mm and bores with diameters of 5-40 mm are known.

Figure 5:
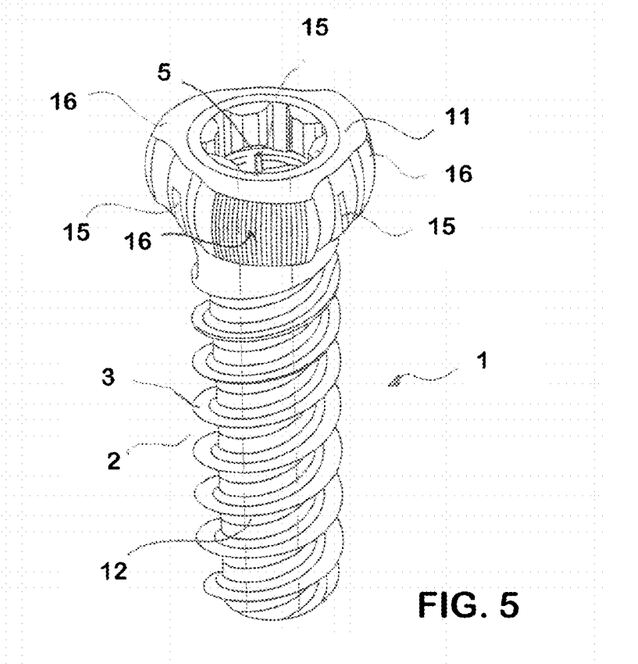
FIG. 5 shows a schematic view of a fixation device according to the invention designed as a screw.

FIG. 5 shows a three-dimensional representation of a fixation device designed as a screw 1. The main body 11 according to FIG. 1 is adjoined by a screw shank 2, which is provided with a screw thread 3. Except for the bore 12 and the slits 15, the screw is designed in accordance with US 2007/0043366. The screw shank 2 with the thread 3 can have advantageous properties depending on the indication. However, it is also conceivable to omit the screw shank 2 or to design it as a pin without a screw thread.

Figure 6:
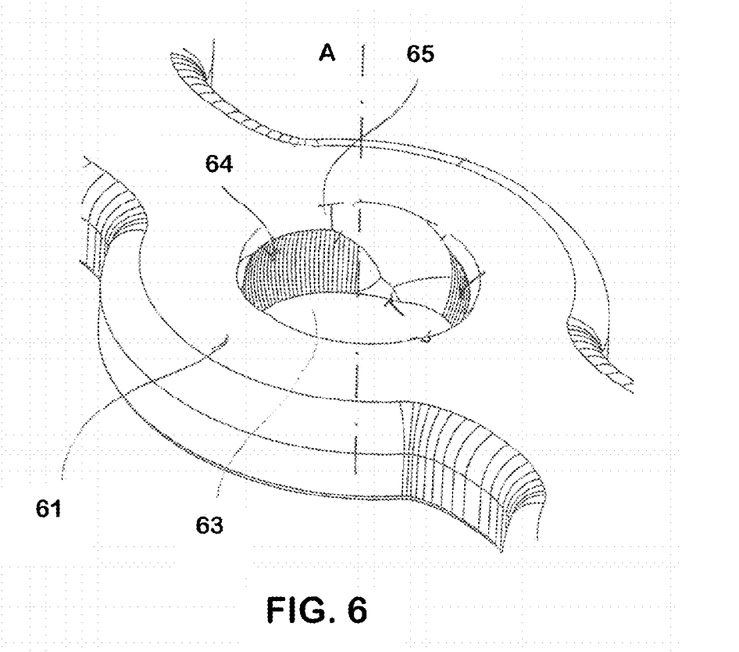
FIG. 6 shows a perspective view of an opening for receiving the fixation device according to the invention.

FIG. 6 shows an example of a seat 63 for the fixation device 10.

The seat 63 has an inner wall 65. The inner wall 65 is provided with projections 64 extending inwards in the radial direction. In FIG. 6, the seat 63 is designed as part of an implant plate 61. The seat is designed in accordance with US 2007/0043366, Of course, corresponding openings can be provided in any desired retaining structures into which elongate elements are intended to be inserted by means of the fixation device.

The plate 61 shown in FIG. 6 with the opening 63 is otherwise identical to the plate shown US 2007/0043366. The content of US 2007/0043366 relating to the seat is also expressly incorporated by cross reference into the present application. In particular, the inner wall 65 has a partially spherical, spiral, parabolic, elliptic or hyperbolic shape in the axial direction A, such that the fixation device with its rounded outer contour 18 can be inserted multi-directionally into the opening 63 and, by turning in the direction U, can be clamped securely in the opening 63.

Figure 7A:
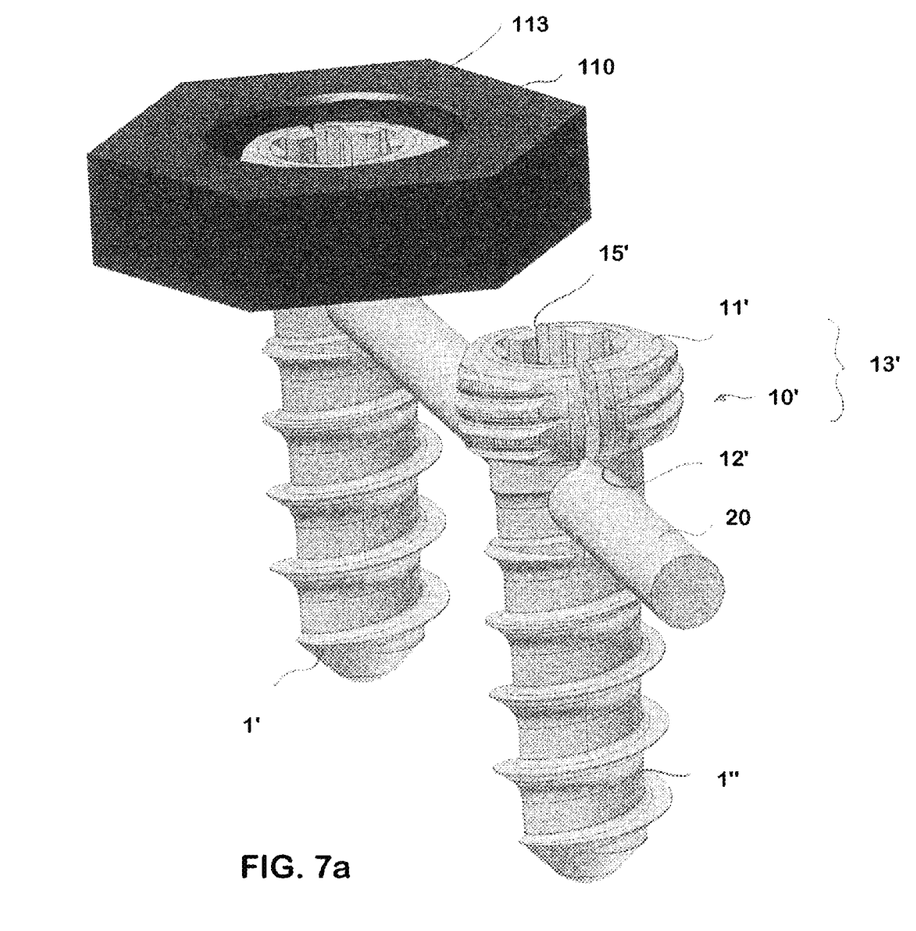
FIG. 7a shows a schematic view of a first alternative illustrative embodiment of a fixation device according to the invention.

FIG. 7a is a schematic view of an alternative embodiment of a fixation device according to the invention. The fixation device according to FIG. 7a is designed as a screw F. In the area of the screw head 10', the screw 1' has a main body 11'. The main body 11' is provided with a slit 15' extending in the axial direction of the screw F. A clamp area 13' is formed by the slit 15'. The main body 11' has a similar design to the main body shown in FIGS. 1 to 4. By inserting the main body 11' into a seat 113 of a retaining structure designed as locking element 110, and by turning it, the main body 11' can be compressed in a plane perpendicular to the axis of the screw 1'. That is to say, the width of the slit 15' is thus reduced. A wire 20, inserted into an opening 12' extending transverse to the screw axis, is thus securely clamped in a direction transverse to the screw axis. It is unimportant here that, seen in the axial direction, the opening 12' is arranged underneath the clamp area 13'. The arrangement shown in FIG. 7a can be used, for example, for distraction if, instead of a wire 20, a two-piece elongate element with inner thread and outer thread meshing on each other is used.

Figure 7B:
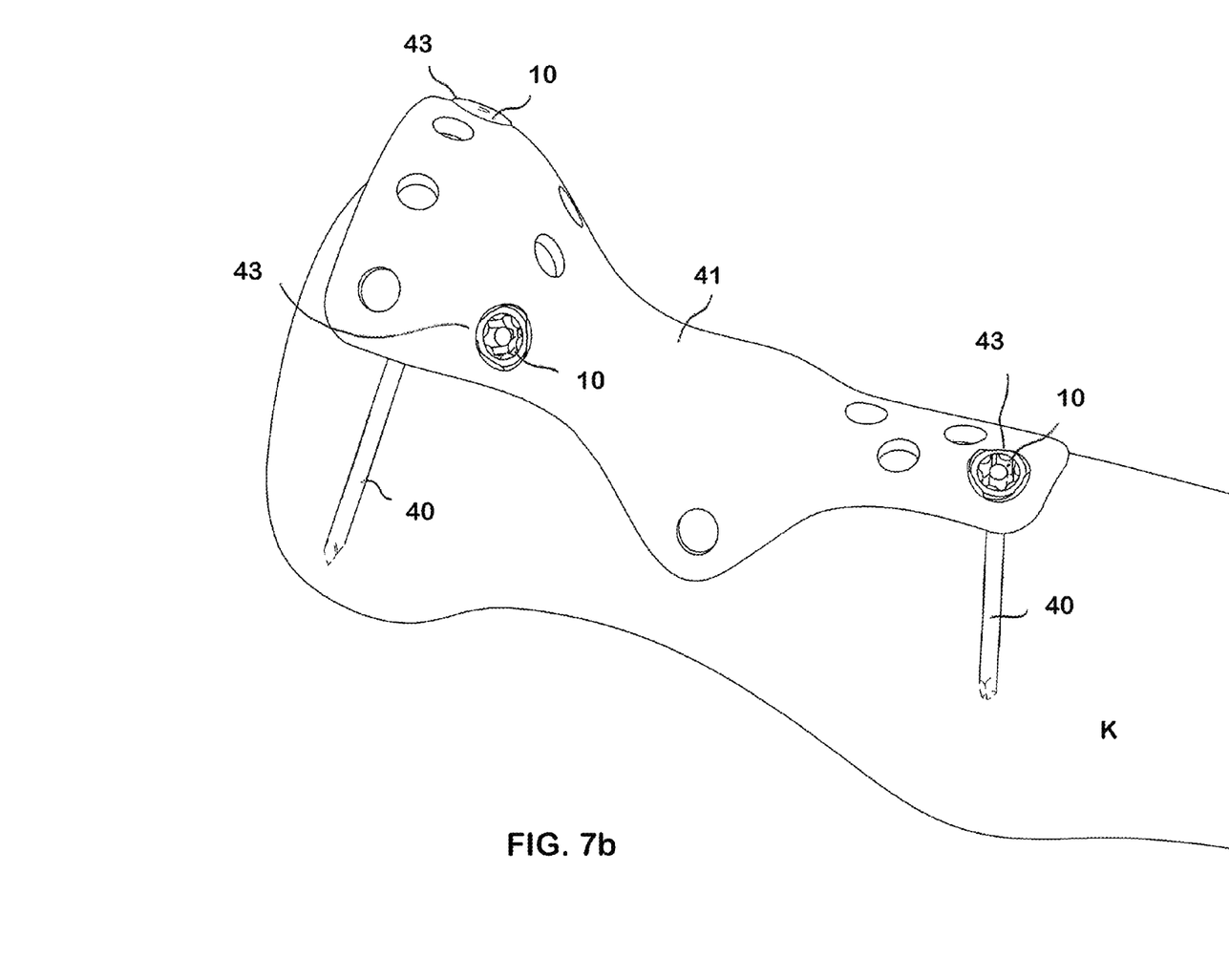
FIG. 7b shows a schematic view of another alternative illustrative embodiment of a fixation device according to the invention.

FIG. 7b shows another alternative embodiment. An implant plate 41 is used as internal fixator for the head of a radius K. For this purpose, wires 40 introduced into the bone K are secured in openings 43 of the plate 41 by means of the fixation devices 10 described above. The fixation devices 10 permit an axial fixation of the wires 40. At the same time, the wires can be inserted at different angles relative to the surface of the plate and can be locked in their angle position. FIG. 7b shows an inner contour for receiving a tool, typically a screwdriver. With this tool, the fixation device 10 can be subjected to a torque, turned, and thereby clamped.

Figure 8:
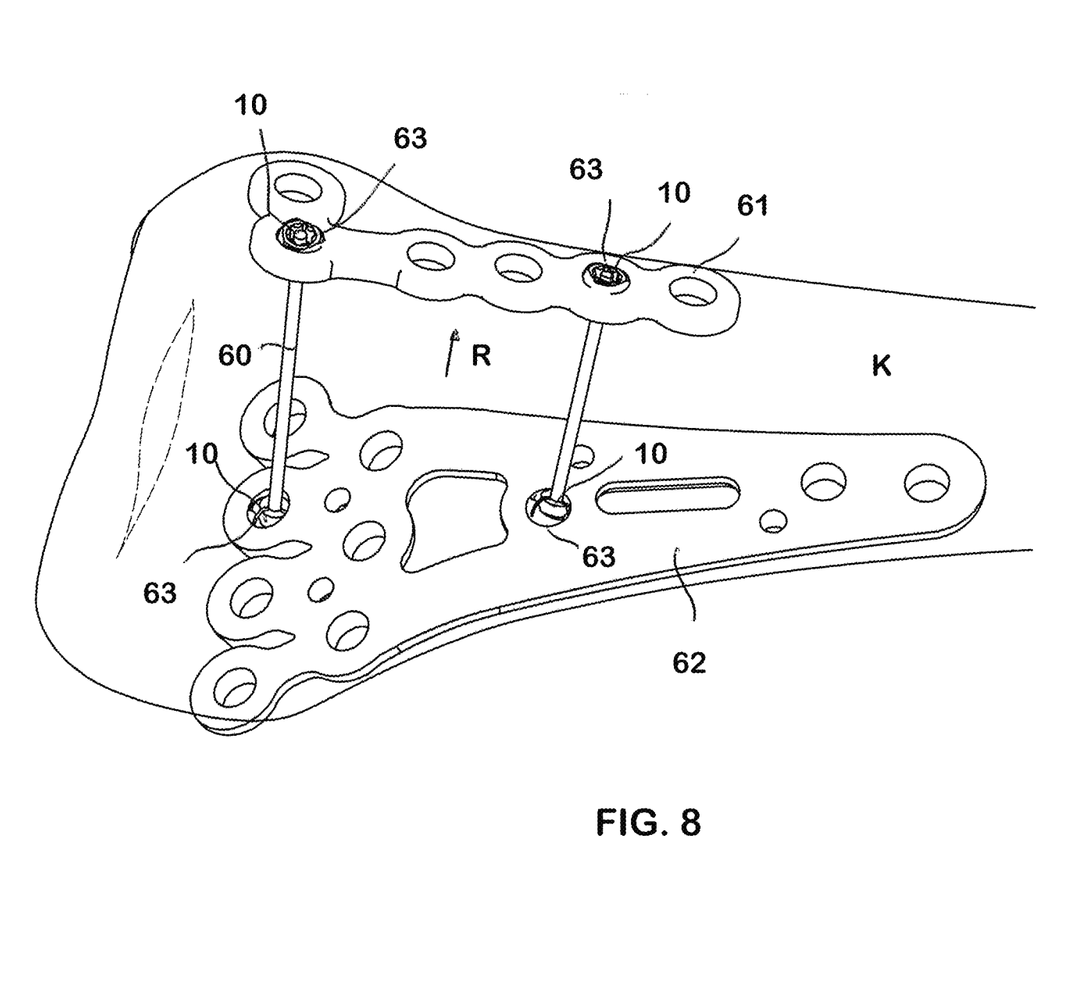
FIG. 8 shows a schematic view of an osteosynthesis set made up of two implant plates.

FIG. 8 shows another possible use of a fixation device according to the invention. Two implant plates 61, 62 are positioned on two sides of a bone K. Two wires 60 are introduced through the bone and are guided through corresponding bores 63 in the implant plates 61, 62. By means of the fixation devices 10 described above, the wires 60 are secured at stable angles in the bores 63. The direction of the wires 60 can be selected freely, by virtue of the free positioning described above. By means of the wires 60, the two implants 61, 62 are connected to each other along the wires 60 in the area of the openings 63 and are thereby stabilized. In this way, a force can be applied, even when the bone substance is not present in sufficient quantity or quality to receive a conventional bone screw.

Figure 9A:
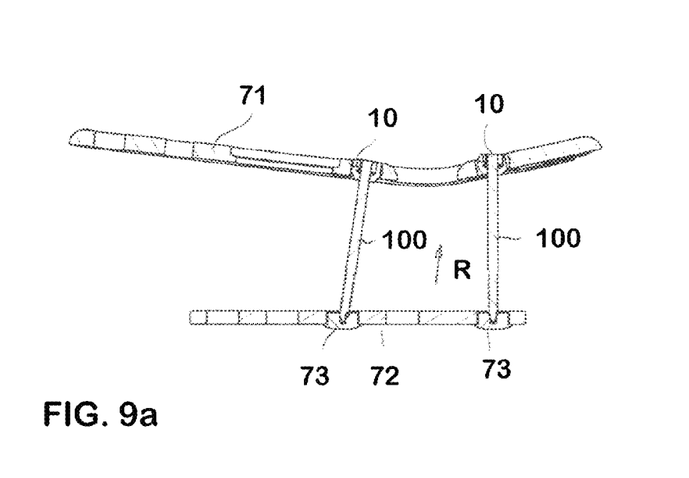
FIGS. 9a and b show alternative embodiments for an osteosynthesis set with two implant plates.
Figure 9B:
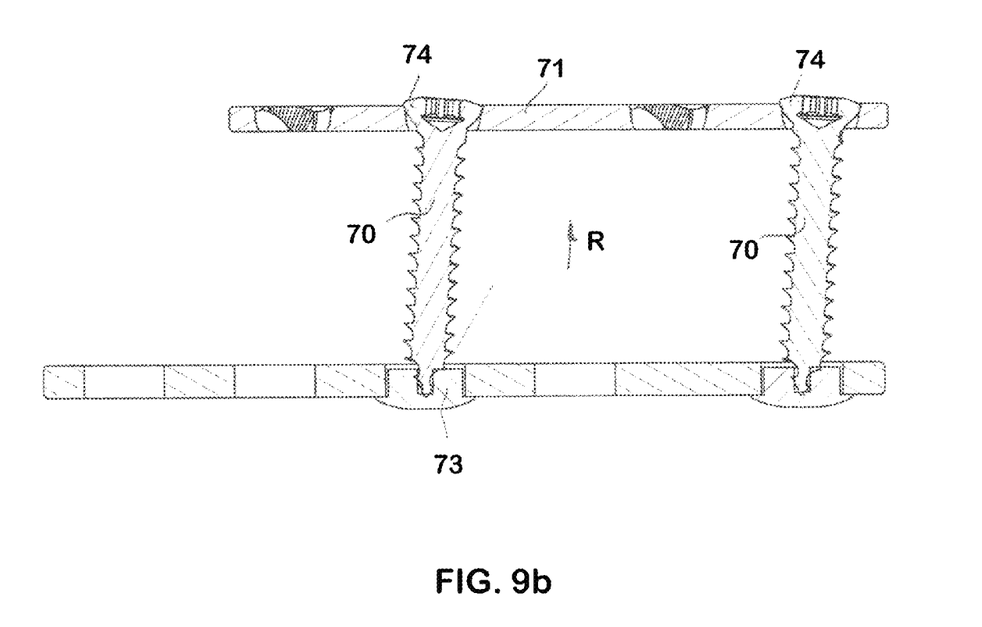

The osteosynthesis set shown in FIG. 8, composed of the plates 61, 62, the wires 60 and the fixation devices 10, allows such implants also to be used in osteoporotic bone for example. FIGS. 9a and 9b show alternative embodiments of such osteosynthesis sets.

FIG. 9a shows an alternative illustrative embodiment of an osteosynthesis set. According to FIG. 9a, two implant plates 71, 72 are connected by wires 100. In the same way as is shown in FIG. 8, each wire 100 is fixed in a seat of one implant plate 71 by means of a clamping device 10. The fixation is effected largely in the manner explained with reference to FIG. 8. In the area of the second implant plate 72, the wire 100 has a thread. A nut 73, e.g. of PEEK, is screwed onto the thread and thus fixes the wire 100 in the area of the second implant plate 72. With such an arrangement too, stabilization can be achieved in direction R, where R does not have to be oriented perpendicular to the plane of the plate.

In FIG. 9b, two implant plates 71, 72 are connected to each other by screws 70. A nut 73 or a small disc with an opening is connected to the end of the screw 70 in the area of one plate 72. The screws 70 are supported with their screw heads 74 on the other plate 71. With this stabilization too, a connection of the implant plates 71, 72 in direction R can be achieved, where R does not have to be perpendicular to the plane of the plate.

Nut is understood here in particular as any type of abutment for the wire. The nut does not necessarily have to be arranged parallel to the plane of the plate. The nut can also have a certain pivoting range. The nut can also be able to be locked. Finally, the nut does not necessarily need to have an opening. A self-drilling wire tip can also drill itself a hole. In addition, the nut can also be preassembled in the plate.

To connect the plates according to FIGS. 7, 7b, 8, 9a and 9b and to stabilize the fragment positions, a wire has to be fitted. For this purpose, a targeting device is used which threads the wire into the start hole and target hole. After the wire has been introduced, the line of connection between these two points corresponds to the wire axis. The clamp elements are then engaged and, by turning them in the circumferential direction U, are blocked in the opening. A pivoting of the fixation device 10 is possible on account of the rounded outer contour, seen in the axial direction, but is limited by the geometry of the implant plates 61, 62 to a certain angle range, typically of at most ±15°.

By means of this pivotability, the plates can be positioned exactly according to the anatomical conditions, without having to take into account the subsequent connection of the plates. In non-multidirectional and non-pivotable systems, compromises would have to be made when adapting them to the anatomical conditions.

Figure 10:
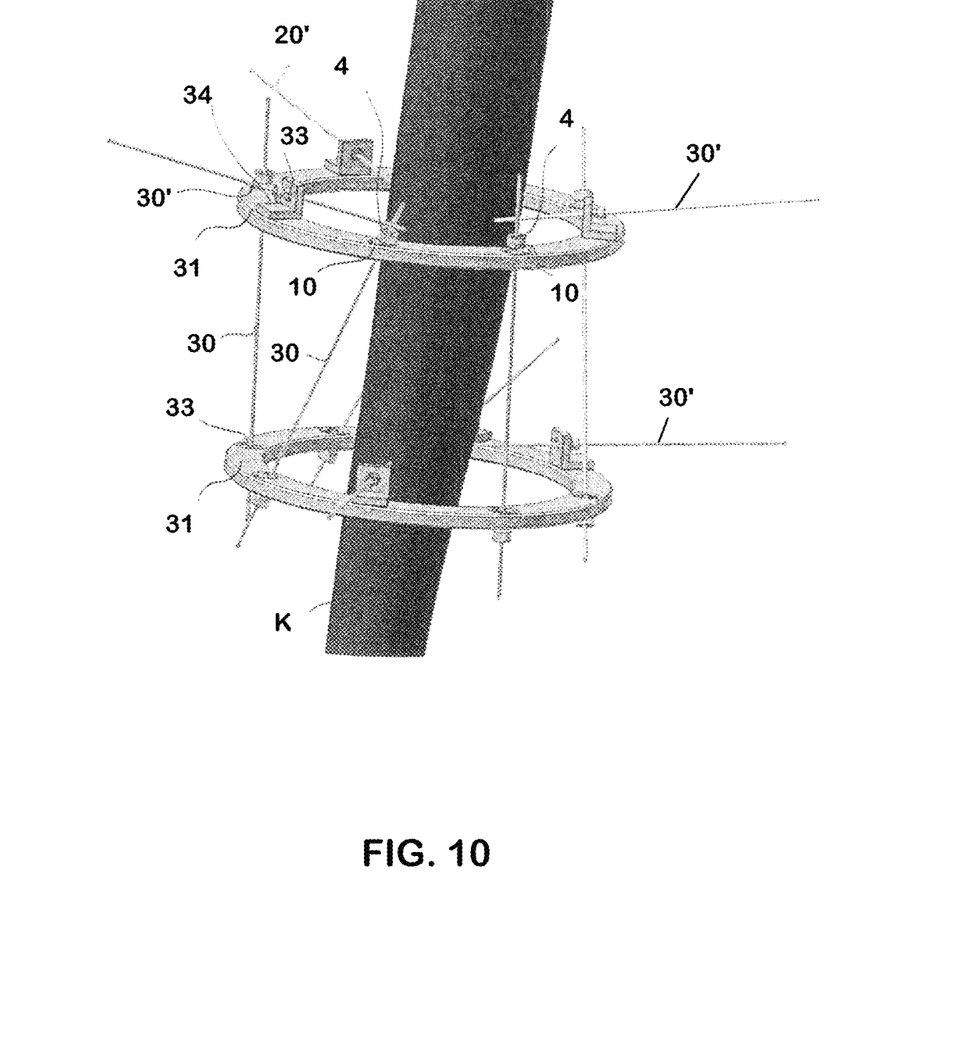
FIG. 10 shows a schematic view of the use of a fixation device according to the invention in an external fixator.

FIG. 10 is a schematic view of the use of fixation devices according to the invention in an external fixator. The external fixator, typically for a humerus, has two rings 31. The rings 31 are intended to be stabilized relative to each other by wires 30. At the same time, the structure composed of the two rings 31 and the wires 31 extending approximately in the direction of the bone K is intended to be fixed to the latter by wires 30' extending perpendicular to the bone. In order to secure the wires 30, 30' in the rings, fixation devices 10 are fitted in openings 33 of the rings or in openings 33 of auxiliary elements 34 mounted on the rings. The fixation devices 10 and the openings 33 are designed as described above. In addition, the fixation devices 10 can be provided with an extension 4, which is used for receiving a tool or for (manual) manipulation.

Figure 11:
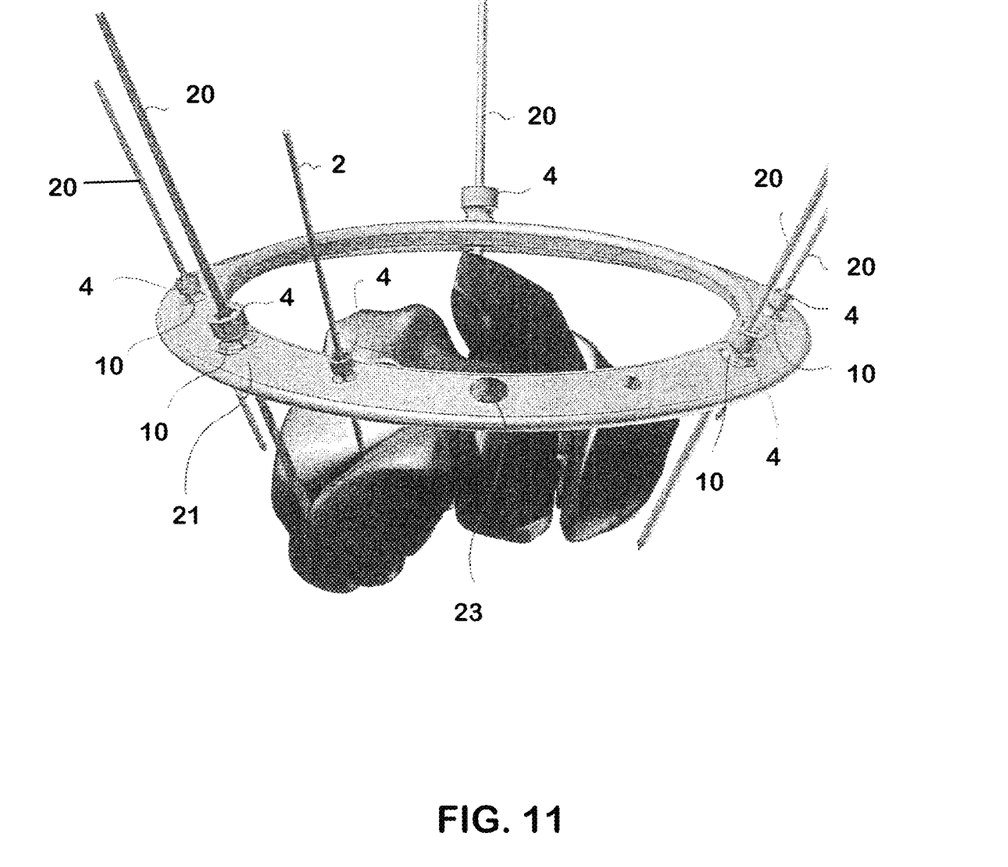
FIG. 11 shows a schematic view of the use of fixation devices according to the invention as temporary intraoperative fixation.

FIG. 11 is a schematic view of a use of the fixation device 10 according to the invention for temporary intraopertaive fixation of a metacarpal. A fixation ring 21 bears on the hand or sweeps across it and is secured to the operating table, e.g. with a fixation device as described above. Fixation wires 20 serve for temporary fixation. The wires 20 are guided through the bore 12 (see, for example, FIGS. 2a and 2b) of the fixation device 10. The fixation devices 10 are screwed into corresponding openings 23 on the fixation ring 21. By turning the fixation device in the circumferential direction U (see also FIG. 3), the fixation devices 10 can be fixed and radially compressed in the openings 23. In this way, the wire 20 is fixed in the axial direction in the fixation device 10, and the fixation ring is also fixed against tilting. The openings 23 have a similar design to the opening shown in connection with the implant plate in FIG. 6. Depending on the application, different sizes of fixation devices 10 can be used.

FIGS. 12 to 19 show various embodiments of elongate elements that can be inserted into the fixation device 10 according to the invention.

FIG. 12 shows schematically a simple wire 20 without any defined contouring of the surface.

Figure 13:
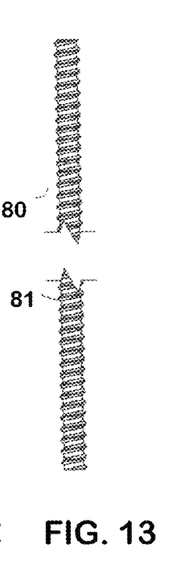

FIG. 13 shows a wire 80 which is provided with a thread 81 along its entire length. Typical applications are, for example, K-wires with a short thread (ca. 20 mm) or with a thread along the whole length. The thread at the tip can be used, for example, to secure a bone fragment against axial displacement on the K-wire. The thread on the entire shaft additionally represents an inexpensive structuring transverse to the longitudinal axis, which can additionally serve to increase the retention force. Instead of a structuring of the surface in the form of a thread 81, knurls extending in the longitudinal direction or in the transverse direction are also conceivable.

Figure 14:
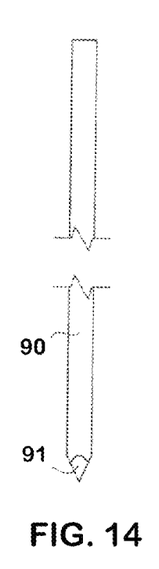

FIG. 14 shows a wire-like element 90 which is provided at its end with a trocar bevel 91.

Figure 15:
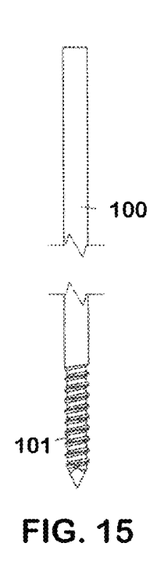

FIG. 15 shows a wire-like element 100 which is provided with a thread 101 only at its tip.

Figure 16:
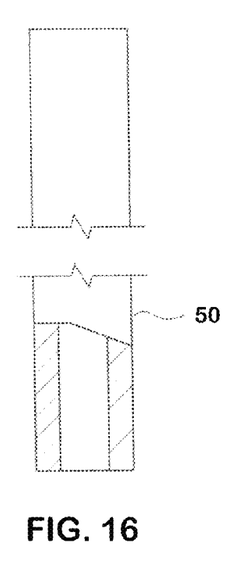

FIG. 16 shows an endoscopy tube 50. An elongate element of tubular shape, as shown in FIG. 16, can also be used in connection with a lancet bevel.

Figure 17:
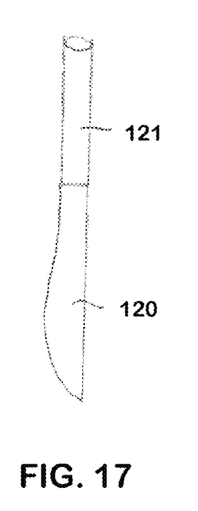

FIG. 17 shows a scalpel 20 which can be secured with its shaft 121 in a fixation device according to the invention.

Figure 18:
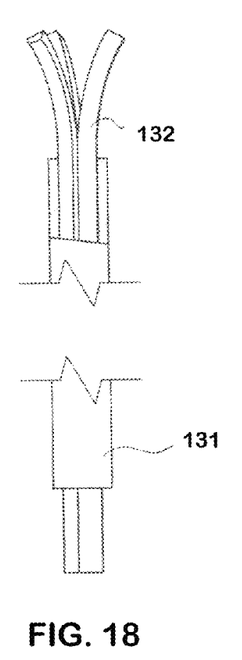

FIG. 18 shows a tubular element 131 which is used to receive a wire bundle 132. In osteoporotic bone of the upper arm, there is a danger of the joint surface collapsing. If the element 131 is fixed in a plate anchored on the shaft of a bone, the ends of the wire bundle can support the osteoporotic bone in the area of the joint surface from the inside. The tubular element then assumes the function of an elongate element, which is fixed in a fixation device 10 (see, for example, FIGS. 1 and 2) of the kind described above. It is also conceivable to provide the tube with a suitable outer contour (not shown), such that the tube meets the object of a fixation device according to the invention for holding the wire bundle.

However, for this purpose it is also possible to use a K-wire with a large end face with an element that folds open or a slotted wire.

Figure 19:
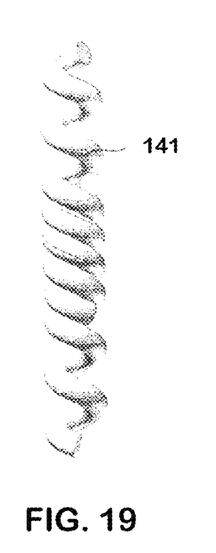

FIG. 19 shows a spring-like element 141. The spring-like element 141 is composed of two interconnected helical springs. As spring element it is also possible to use leaf springs, helical springs, or also a spring made up of two spiral springs pushed one inside the other.

The elongate elements are made of suitable materials depending on the particular application. Typically, titanium can be used for implantable elements. Other materials that can conceivably be used are stainless materials, shape-memory alloys, elements of superelastic materials, or also plastic.

What is claimed is:

1. A fixation device for fixing an elongate element in a seat of a retaining structure, said fixation device comprising a body having:
   (a) a bore extending along a longitudinal axis and defining an opening for receiving the elongate element,
   (b) a clamping portion which is radially deformable so that the opening can be reduced in size to grip the elongate element, and
   (c) an outer surface having at least one protrusion which can be brought to bear against a corresponding projection in the seat by only rotating the body about the longitudinal axis in and relative to the seat, to deform the clamping portion radially inward against the elongate element,
   wherein the protrusion has a rounded outer contour, when viewed in a direction perpendicular to direction of the longitudinal axis, so that the direction of said longitudinal axis and the elongate element can be adjusted over a range of angles by tilting the body in the seat,
   the outer contour of the protrusion at least partially widens radially, seen in a circumferential direction, and
   in a region of the outer contour, viewed in an azimuth plane perpendicular to the longitudinal axis, a distance of the outer contour increases outward from the longitudinal axis as a function of an angle of revolution about the longitudinal axis.

2. The fixation device according to claim 1, wherein the clamping portion of the body has at least one longitudinally extending slot to increase the radial deformability of the clamping portion.

3. The fixation device according to claim 1, wherein the body has a drive structure for receiving a tool for turning the body, about said longitudinal axis, in the seat.

4. The fixation device according to claim 1, wherein the opening has a textured inner surface for enhancing grip on the elongate element.

5. The fixation device according to claim 1, wherein the elongate element is selected from the group consisting of a wire, a rod, a pin, and a profile.

6. The fixation device according to claim 1, wherein the elongate element has a textured external surface for enhancing the grip of the body on the elongate element.

7. The fixation device according to claim 6, wherein the textured external surface is a thread.

8. The fixation device according to claim 1, wherein the elongate element has either a self-cutting or a self-drilling external thread.

9. The fixation device according to claim 1, wherein the outer contour of the protrusion at least partially has a spherical, paraboloidal, ellipsoidal or hyperboloidal outer contour.

10. The fixation device according to claim 1, wherein the outer surface has three protrusions which are distributed uniformly about a circumference of the body.

11. A surgical assembly comprising
at least one implant plate having a seat with an inwardly projecting wedging portion;
at least one body having a clamping portion sized to fit within said seat; and
at least one elongate element for connecting the plate to another structure; said body having:
(a) a bore defining an opening with a longitudinal axis, for receiving the elongate element,
(b) a clamping portion which fits within said seat and is radially deformable so that the opening can be reduced in size to grip the elongate element, and
(c) an outer surface having at least one protrusion which can be brought to bear against a corresponding projection in the seat by only turning the body in the seat about the longitudinal axis, to deform the clamping portion radially inward against the elongate element,
wherein the protrusion has a rounded outer contour when viewed in a direction perpendicular to direction of the longitudinal axis, so that the direction of said longitudinal axis and thus the elongate element can be adjusted over a range of angles by tilting the body in the seat,
the outer contour of the protrusion at least partially widens radially, seen in a circumferential direction, and
in a region of the outer contour, viewed in an azimuth plane perpendicular to the longitudinal axis, a distance of the outer contour increases outward from the longitudinal axis as a function of an angle of revolution about the longitudinal axis.

12. The surgical assembly according to claim 11, further comprising a second implant plate, wherein each implant plate is provided with at least one seat for receiving a connector, and further comprising a connector which can be inserted into a seat of each of the implant plates, wherein the implant plates can be connected to one another and stabilized by the connector.

13. The surgical assembly according to claim 11, wherein the implant plate is formed in plural sections, each section having at least one seat, and further comprising a connector which is insertable into a seat of each of the sections, to join the sections.

14. The surgical assembly according to claim 12, wherein the connector comprises an at least partially threaded elongate element.

15. The fixation device according to claim 1, wherein the body and thus the elongate element can be fixed in the seat at any angle over said range of angles.

16. The surgical assembly according to claim 11, wherein the protrusion can be brought to bear against the projection in the seat by only turning the body about the longitudinal axis in and relative to the seat, to deform the clamping portion radially inward against the elongate element.

17. The fixation device according to claim 1, wherein the elongate element is selected from the group consisting of a lancet and a trocar.

\* \* \* \* \*